United States Patent [19]

Dance et al.

[11] Patent Number: 5,078,723
[45] Date of Patent: Jan. 7, 1992

[54] ATHERECTOMY DEVICE

[75] Inventors: Creg Dance, Elk River, Minn.; Kevin Larkin, Marietta, Ga.; Lynn Jabbusch, La Mesa, Calif.; John V. Hoek, Florence, Ky.

[73] Assignee: Medtronic, Inc., Minneapolis, Minn.

[21] Appl. No.: 630,422

[22] Filed: Dec. 19, 1990

Related U.S. Application Data

[63] Continuation of Ser. No. 350,679, May 8, 1989, abandoned.

[51] Int. Cl.$^5$ .............................................. A61B 17/32
[52] U.S. Cl. ................................... 606/159; 606/170; 604/22
[58] Field of Search .................. 128/751–755; 604/22, 95, 164, 264, 274; 606/159, 170, 171

[56] References Cited

U.S. PATENT DOCUMENTS

| | | | |
|---|---|---|---|
| 2,701,559 | 2/1955 | Cooper | 128/2 |
| 2,850,007 | 2/1958 | Lingley | 128/2 |
| 3,064,651 | 11/1962 | Henderson | 128/221 |
| 3,082,805 | 3/1963 | Royce | 146/68 |
| 3,683,891 | 8/1972 | Eskridge et al. | 128/751 |
| 3,732,858 | 5/1973 | Banko | 128/2 B |
| 3,749,085 | 7/1973 | Willson et al. | 128/2 B |
| 3,800,783 | 4/1974 | Jamshidi | 128/2 B |
| 3,945,375 | 3/1976 | Banko | 128/6 |
| 3,976,077 | 8/1976 | Kerfoot, Jr. | 128/305 |
| 4,007,732 | 2/1977 | Kvavle et al. | 128/2 B |
| 4,177,797 | 12/1979 | Baylis et al. | 128/754 |
| 4,273,128 | 6/1981 | Lary | 128/305 |
| 4,368,730 | 1/1983 | Sharrock | 604/164 X |
| 4,490,139 | 12/1984 | Huizenga et al. | 604/57 |
| 4,512,344 | 4/1985 | Barber | 128/305 |
| 4,603,694 | 8/1986 | Wheeler | 606/171 |
| 4,646,719 | 3/1987 | Neuman et al. | 128/1 D |
| 4,646,736 | 3/1987 | Auth | 606/170 X |
| 4,646,738 | 3/1987 | Trott | 606/170 |
| 4,653,496 | 3/1987 | Bundy et al. | 128/751 X |
| 4,669,469 | 6/1987 | Gifford, III et al. | 606/170 X |
| 4,686,982 | 8/1987 | Nash | 128/305 |
| 4,696,667 | 9/1987 | Masch | 606/170 X |
| 4,706,671 | 11/1987 | Weinrib | 128/348.1 |
| 4,732,154 | 3/1988 | Shiber | 606/159 X |
| 4,745,919 | 5/1988 | Bundy et al. | 128/753 X |
| 4,765,332 | 8/1988 | Fischell et al. | 128/305 |
| 4,771,774 | 9/1988 | Simpson et al. | 128/305 |
| 4,781,186 | 11/1988 | Simpson et al. | 606/171 |
| 4,784,636 | 11/1988 | Rydell | 604/22 |
| 4,794,931 | 1/1989 | Yock | 128/660.03 |
| 4,819,634 | 4/1989 | Shiber | 128/305 |
| 4,842,579 | 6/1989 | Shiber | 604/22 |
| 4,844,064 | 7/1989 | Thimsen | 606/170 X |
| 4,850,957 | 7/1989 | Summers | 604/22 |
| 4,883,458 | 11/1989 | Shiber | 606/159 X |
| 4,898,575 | 2/1990 | Fischell et al. | 606/159 X |

Primary Examiner—Robert A. Hafer
Assistant Examiner—Kevin G. Rooney
Attorney, Agent, or Firm—Sandra S. Schultz; Robert J. Klepinski

[57] ABSTRACT

A device for removing stenosis from arteries includes a catheter body for delivering a cutter to the area of the stenosis. A screw is mounted on the distal end of the body for entering and fixedly holding the stenosis. An annular cutting means is moved forward around the screw to cut the stenosis which is held by the screw. The catheter is then removed with the cut stenosis trapped inside the cutter.

1 Claim, 2 Drawing Sheets ns/350,679 filed May 8, 1989, now abandoned.

ATHERECTOMY DEVICE

This is a continuation of application Ser. No. 07/350,679 filed May 8, 1989, now abandoned.

BACKGROUND OF THE INVENTION

1. Field of the Invention

The present invention relates to devices for removing obstructions from blood vessels.

2. Prior Art

The closing of blood vessels poses serious circulatory problems. A closure is generally referred to as a stenosis. Stenoses can result from many various types of tissue growth. Some stenoses may be calcified. Others consist of fibrous tissue. A great variety of events can cause stenoses and the resulting tissue can be of many forms.

A stenosis can prevent adequate blood flow to downstream parts of the body. An example of paramount importance is a stenosis in a coronary artery which provides blood to the heart muscle. Lack of blood to this muscle can cause an infarction or other heart problems.

Many methods have been tried to overcome this problem. Traditionally, surgery was performed to add bypass path around the obstruction. Balloon angioplasty was later developed to partially open occlusions without open heart surgery.

Another technique is to cut away the occluding tissue, rather than bypassing it or working around it. This is sometimes known as atherectomy.

A variety of atherectomy devices have been proposed. One example is the cutting device disclosed in U.S. Pat. No. 4,653,496 to Bundy et al issued Mar. 31, 1987. This device includes a helical hollow cutting tool with a sharpened edge which slices a stenosis. A cutting cannula also assists in cutting the stenosis.

Other devices, such as disclosed in the various Nash and Kensey patents, attempt to pulverize the stenosis. One example, U.S. Pat. No. 4,686,982 to Nash has a rotating cutting head which whips water at the stenosis. The combination of the cutting head and swiftly propelled water is claimed to demolish the stenosis into particles sufficiently small that they can safely flow through the bloodstream.

Of course, it is important that dangerous particles do not escape into the bloodstream during the atherectomy process. What is needed is a device that both safely cuts the stenosis and removes it from the bloodstream so that normal flow is restored and no dangerous particles escape.

The present invention is designed to improve on the prior art in that it engages a portion of the stenosis and holds it while the stenosis is cut. The cut portion of the stenosis is trapped within the device which can be withdrawn from the vessel to minimize the chance of any loose particles endangering the patient.

SUMMARY OF THE INVENTION

The present invention includes a generally cylindrical torque-transmitting body which is inserted in a blood vessel in which there is a stenosis, the body having a distal end and a proximal end. Non-cutting engagement means are mounted on the distal end for engaging the stenosis. Movable cutting means are mounted on the distal end of the body for longitudinal movement in the distal and proximal directions. The cutting means preferably annularly surrounds the engagement means. Control means are mounted on the proximal end of the catheter for advancing the cutting means over the engagement means to cut the stenosis that is held by the engagement means.

The atherectomy device control means preferably includes first rotation means mounted on the proximal end of the body for rotating the engagement means to engage the stenosis and second rotation means for rotating the cutting means.

In the preferred embodiment, a torque cable is constructed of first and second helically tightly wound wires; the first wire being wound in a first angle and the second wire being wound in a second opposite angle so that the resulting cable transmits torque from the proximal end to the distal end. A knob is preferably attached to the proximal end of the torque cable for rotation of the cable.

The outer, or second, wire of the torque cable is processed, such as by spreading coils apart or by attaching a spread coil, to form an open non-cutting helix for a portion of the distal end of the torque cable. A leading edge of the resultant screw-shaped distal portion of the second wire is sharpened to ease entry into stenosis. When the cable is advanced against a stenosis and the knob is turned, the helical distal end of the torque cable is screwed into the stenosis.

A cutter cable, constructed of first and second helically wound together wires, is constructed in the same manner as the torque cable. The cutter cable is mounted slideably over the torque cable for longitudinal and rotational movement relative to the torque cable. A cutter head is mounted on a leading edge of the cutter coil for cutting stenosis. A control is mounted on the proximal end of the body, encompassing the torque cable and the cutter coil. A knob for mounting for rotating the torque cable is rotatably mounted on the control. An advancement means is preferably mounted in a handle of the control and attached to the cutter cable.

In operation, the body is inserted in the blood vessel by conventional means, such as a guiding catheter or guide wire. The body is advanced until the cable distal tip is adjacent to the stenosis. The rotating knob is then turned to screw the distal tip into the stenosis, without cutting loose any tissue. Once the screw has engaged stenosis tissue, the cutter cable is advanced and rotated to cut the stenosis. When the cutter cable is advanced, it encases the cut tissue and the screw of the torque cable. The entire device is then withdrawn from the vessel with the cut stenosis trapped inside the screw and surrounded by the cutter cable.

DETAILED DESCRIPTION OF THE PREFERRED EMBODIMENT

The device 10 comprises a torque cable 12, a cutter cable or ribbon cable 14 and a control handle 16.

Figure 1:
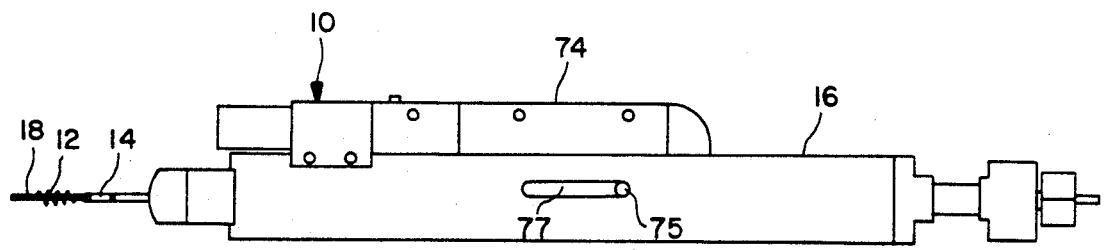
FIG. 1 is a side plan view of the atherectomy device mounted on a guide wire.

In FIG. 1, the device 10 is shown mounted on a guide wire 18, which is conventional. In practice, guide wire 18 is normally fed through the blood vessel and up to the area of the stenosis. The central lumen of device 10 is slid over guide wire 18 up to the stenosis.

Figure 3:
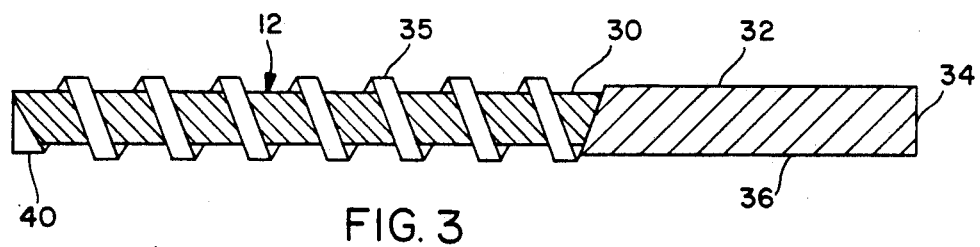
FIG. 3 is an enlarged view of the distal tip of the torque cable of the device of FIG. 1.

The construction of torque cable 12 is illustrated in FIG. 3. A first wire 30 is tightly helically wound at an acute angle to a longitudinal axis of torque cable 12. Second wire 32 is wound at a second opposite angle. First wire 30 is wound so that it forms central lumen 34. In the preferred embodiment, the first and second wires 30 and 32 are made of 304 V stainless steel. The size of first wire 30 is preferably 0.006 inches. The diameter of second wire 32 is preferably 0.012 inches. Lumen 34 is preferably sized so that torque cable 12 will slide easily over a 0.014 inch guide wire system.

The torque cable 12 formed by wires 30 and 32 has great torsional rigidity. That is, torque is easily and completely transferred from the proximal end of torque cable 12 to the distal end of torque cable 12. However, cable 12 has great flexibility in all other directions.

A screw 35 is attached to cable 12. Second wire 32 has a tightly wound proximal area 36. Screw 35 may be formed integral with area 36 and then have its coils of wire 32 spaced about approximately three coil widths apart. The distal spaced apart area or screw 35 of wire 32 is approximately 1 inch long in the preferred embodiment. In the preferred embodiment, screw 35 is formed separately and brazed to portion 36.

Screw 35 has a leading edge 40 which is sharpened for facilitating its entry into a stenosis. Screw 35 does not have a cutting edge which cuts stenosis free. Rather, sharpened edge 40 of the screw 35 is turned in the stenosis as torque cable 12 is rotated, in this case in a clockwise direction. Wire 22 and screw 35 are preferably formed of cylindrical wire, which is ground down on the exterior of the coil to a semi-circular cross-section. The exterior of coil 32 is a generally smooth cylinder. The semi-circular cross-section provides a good bite into the stenosis as the screw 35 anchors itself. In another embodiment, screw 35 is made of wire with a circular cross section.

Figure 4:
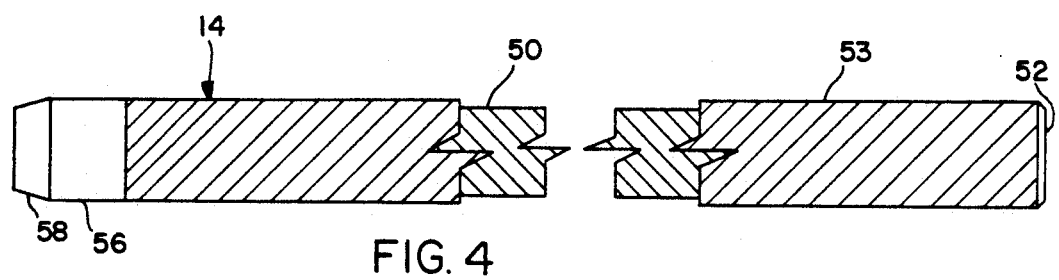
FIG. 4 is an enlarged, partially cutaway view of the distal end of the flat ribbon cable of FIG. 1.

A distal portion of ribbon cable 14 is illustrated in FIG. 4. Cable 14 is formed by winding helically a tight wind of flattened ribbon 50 made of 304 V stainless steel. Ribbon 50 is wound to form a second lumen 52 which is sized to slideably fit over torque cable 12. Ribbon 53 is wound at an opposite angle to ribbon 50, over ribbon 50.

Cutter head 56 is preferably brazed to ribbon 53. The cutter head 56 carries a cutting edge 58 which is generally circular.

In operation, cable 14 is slideably mounted over torque cable 12. Torque cable 12 is advanced to contact a stenosis. Torque cable 12 is then rotated so that leading edge 40 enters the stenosis and the screw 35 is turned into the stenosis. This action firmly engages the screw 35 within the stenosis. The stenosis remains in place.

Cutter cable 14 is then advanced and preferably rotated over the screw 35 to cut the stenosis and trap the cut material between screw 35 and cable 14. Cutter head 58 and cable 12 interact much like a pair of scissors, although only cutter head 58 is sharpened. The device 10 is then withdrawn from the vessel with the cut stenosis material trapped inside.

Unlike prior art devices which use a cutting auger, the present invention works in the manner of a corkscrew. The tip of the screw is sharpened only to allow access into stenosis material. The auger is not designed to cut free any portion of the stenosis. Rather, as described above, the screw engages the material and holds it in position relative to the device body for cutting.

Cutting occurs when cable 14 is advanced over the screw. Cutting edge 58 cuts the stenosis. Once cut, stenosis material is still trapped by the screw. The body of the device is then withdrawn with the material safely encased.

Unlike prior art devices which have used various forces such as water or cutting edges to free material from a stenosis, the present device does not cut material free until it is trapped. Whereas prior art taught such techniques as suction or auger action to work material back through the device after it was cut, the present invention is designed to firmly engage the material, cut it, and then trap it for positive removal.

Figure 2:
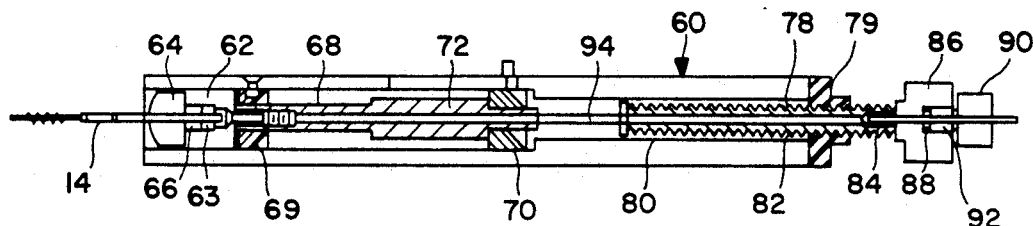
FIG. 2 is a cross sectional view of the handle of the device taken on line 2—2 of FIG. 1.

The control means preferred for operation of the atherectomy device is illustrated in FIG. 2. The control means includes a handle 60. Handle 60 is a generally cylindrical body made of Delrin, which has an irregular lumen through it for the mounting of control parts. Mounted in the distal end of handle 60 is a knob 62. Knob 62 has a female threaded opening in the distal direction. A silicone seal 63 is mounted within knob 62. A knob 64 with a male threaded portion 66 screws into knob 62. The cutter cable 14 proximally terminates at the connection of knob 64 and knob 62. As knob 64 is tightened down, it engages cable 14 in a clutch-like fashion and secures it to handle 60. Inner torque cable 12 continues through knob 64 and knob 62 and through the remainder of handle 60 out its proximal end.

A pinion wire 68 is attached to the proximal end of cutter cable 14 by means of knobs 62 and 64 with seal 63. Pinion wire 68 is rotatably mounted within handle 60 on bushings 69 and 70. Bushing 69 is fixedly mounted in handle 60. Busing 70 is slidably mounted within handle 60. The proximal end of pinion wire 68 includes a section of toothed gear 72. As the gear 72 is rotated, cutter cable 14 is rotated to cut stenosis. In the embodiment illustrated, a motor 74 is mounted to handle 60. Motor 74 is operably connected to gear 72. As motor 74 rotates gear 72, it rotates cutter cable 14.

Motor 74 may be any suitable small electric motor, preferably battery powered. The motor chosen for the illustrated embodiment is provided by Micromo.

A knob 75 is fixedly mounted on bushing 70. Knob 75 protrudes through a slot 77 in housing 16. As knob 75 is advanced in the distal direction, bushing 70, and therefore pinion wire 68, are moved distally. This advances cutter cable 14 over cable 12.

Torque cable 12 is fixedly mounted in a screw 78, which is threadably mounted in the proximal end of handle 60 by means of nut 79. Screw 78 includes a distal portion 80 which is unthreaded, a central portion 82 which is threaded, and a proximal portion 84 which is unthreaded. A control knob 86 is fixedly attached to the proximal end of screw 78. The seal 88 is mounted in a female threaded opening in knob 86. A knob 90 has a male threaded portion 92 which is screwed into knob 86 to compress seal 88. There is a central lumen through knobs 86 and 90 through which passes a torque cable 12.

When knob 90 is tightened down against seal 88, it fixedly engages torque cable 12 and makes a complete connected working unit of knob 90, knob 86, screw 78 and torque cable 12.

A section of hypo tube 94 is attached to screw 78. Tube 94 slides within pinion wire 68 to keep cable 12 aligned. When the device is in use, screw 78 is removed generally to the far distal position. This means the portion 80 which is not threaded freely slides within nut 79. In this manner, torque cable 12 can be withdrawn away from the end of cutter cable 14. This allows cutter cable 14 to have a very flexible tip to be used to work up to a stenosis. Then cable 12 is advanced by sliding knob 86 distally until threaded portion 82 reaches nut 79. At this point, knob 86 is rotated so that threaded portion 82 engages nut 79. This rotates screw 35 into the stenosis. After threaded portion 82 is entirely within handle 60, the unthreaded portion 84 is within the threaded area of nut 79 so that torque cable 12 is free to rotate without any additional longitudinal advancement.

Figure 5:
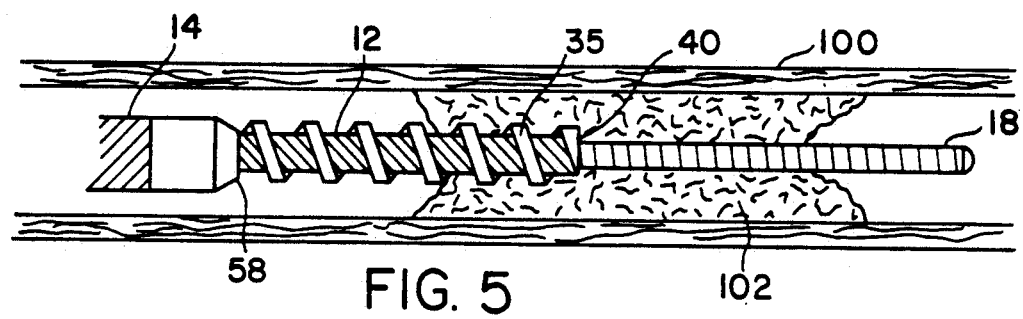
FIG. 5 is a perspective view of the atherectomy device of the present invention entering stenosis.
Figure 6:
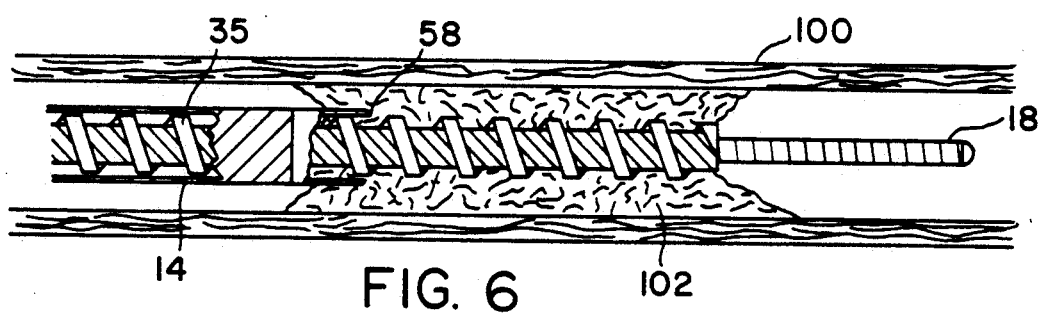
FIG. 6 shows the atherectomy device of FIG. 5 with the cutter advancing.
Figure 7:
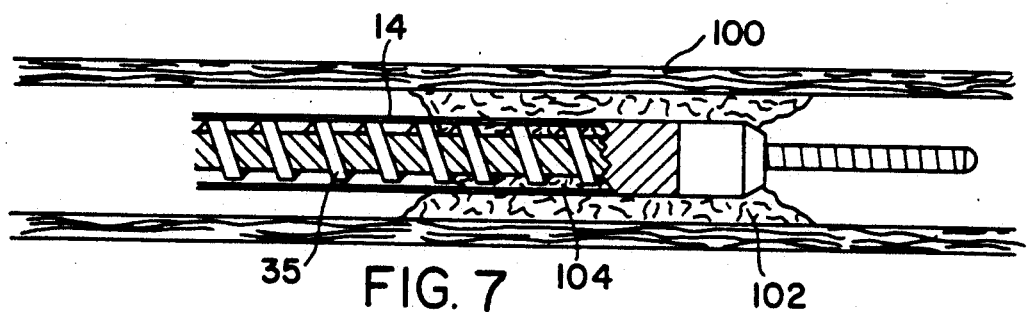
FIG. 7 shows the atherectomy device of FIG. 6 with the stenosis captured within the device.

Operation of device 10 is illustrated in FIGS. 5, 6 and 7 in the process of removing part of stenosis 102. In FIG. 5, device 10 is shown in the position where guidewire 18 has been advanced through stenosis 102. Unlike prior art atherectomy devices, which cannot address stenoses which do not have a functional lumen for passage, device 10 only needs sufficient passage to slide a guidewire, such as 18, through the stenosis. In many cases, a guidewire can be advanced through virtually complete stenosis.

In FIG. 5, screw 35 has been rotated so that its leading edge 40 has entered stenosis 102 and has begun to engage the stenosis 102.

In FIG. 6, screw 35 has been completely advanced through stenosis 102. Cutter cable 14 has been advanced, preferably in rotation, so that its cutting edge 58 cuts a cylinder from stenosis 102. Note that, as shown in Figs. 5 and 6, screw 35 does not noticeably cut free any stenosis 102. As shown in FIG. 6, the screw 35 engages and holds device 10 in position in stenosis 102.

Cutting is performed as cutting edge 58 advances through stenosis 102.

In FIG. 7, cable 14 is shown advanced through stenosis 102. Cutting edge 58 has cut a generally cylindrical portion 104 of stenosis 102 during its advancement. Cut stenosis portion 104 is shown trapped within ribbon cable 14, still engaged by screw 35.

This method of engagement, cutting, and entrapment, minimizes the risk of free pieces of stenosis breaking loose and flowing downstream, which could occlude coronary arteries as they narrow in diameter.

Once stenosis is cut and held, as shown in FIG. 7, device 10 is withdrawn from artery 100 and out of the body. Ribbon cable 14 is withdrawn from around screw 35 and cut stenosis 104 is removed from the screw.

We claim:

1. An atherectomy device comprising:
   a hollow torque cable comprising a first coil of wire wound at a first angle, and a second coil of wire wound concentrically around the first coil at a second angle in an opposite direction;
   the second coil being stretched at its distal end to form a helical screw, the tip segment of the screw portion of second coil being sharpened to facilitate entry of the screw into stenosis tissue;
   a cutter coil slidably mounted concentrically over the torque cable for reciprocal movement in the proximal and distal direction, the cutter coil having a cutting edge mounted on the distal tip of the flat ribbon coil for close scissor-like interaction with the screw;
   control means having rotation means attached to the proximal end of the torque cable for rotating the torque cable to advance the screw into stenosis tissue; and
   cutter advancement means mounted on the cutter coil for moving the cutter coil longitudinally relative to the torque cable.

* * * * *